(12) United States Patent
Lauf et al.

(10) Patent No.: US 12,133,640 B2
(45) Date of Patent: Nov. 5, 2024

(54) ORTHOPEDIC RETRACTOR

(71) Applicant: Life Spine, Inc., Huntley, IL (US)

(72) Inventors: Garrett D. Lauf, Elgin, IL (US); Daniel P. Predick, West Lafayette, IN (US)

(73) Assignee: Life Spine, Inc., Huntley, IL (US)

( * ) Notice: Subject to any disclaimer, the term of this patent is extended or adjusted under 35 U.S.C. 154(b) by 462 days.

(21) Appl. No.: 17/493,384

(22) Filed: Oct. 4, 2021

(65) Prior Publication Data

US 2022/0022861 A1    Jan. 27, 2022

Related U.S. Application Data

(63) Continuation of application No. 16/351,298, filed on Mar. 12, 2019, now Pat. No. 11,134,936.

(60) Provisional application No. 62/641,782, filed on Mar. 12, 2018.

(51) Int. Cl.
*A61B 17/02* (2006.01)
*A61F 2/46* (2006.01)

(52) U.S. Cl.
CPC ........ *A61B 17/0206* (2013.01); *A61B 17/025* (2013.01); *A61B 17/0218* (2013.01); *A61B 2017/0256* (2013.01); *A61F 2/4611* (2013.01)

(58) Field of Classification Search
CPC .................................. A61B 17/02–2017/0275
See application file for complete search history.

(56) References Cited

U.S. PATENT DOCUMENTS

| 7,931,589 | B2 * | 4/2011 | Cohen ................ A61B 17/0206 |
| | | | 600/210 |
| 8,313,430 | B1 | 11/2012 | Pimenta |
| 8,353,826 | B2 | 1/2013 | Weiman |
| 8,357,184 | B2 * | 1/2013 | Woolley .................... A61B 1/32 |
| | | | 606/279 |
| 8,968,363 | B2 | 3/2015 | Weiman et al. |
| 9,381,008 | B2 * | 7/2016 | Thornburg ......... A61B 17/0206 |
| 9,408,598 | B1 * | 8/2016 | Fantini ................. A61B 17/025 |

(Continued)

FOREIGN PATENT DOCUMENTS

| WO | WO-2012/040206 A1 | 3/2012 | |
| WO | WO-2015134367 A1 * | 9/2015 | ......... A61B 17/0206 |

OTHER PUBLICATIONS

International Search Report and Written Opinion in PCT/US2019/021940 dated May 27, 2019.

*Primary Examiner* — Zade Coley
(74) *Attorney, Agent, or Firm* — Foley & Lardner LLP

(57) ABSTRACT

A retractor includes a body, a first handle pivotally coupled to the body, a first attachment assembly comprising a first button configured to allow detachment of a second handle portion from the first handle, a first arm assembly attached to the first handle, a first blade attached to the first arm assembly, wherein the first handle is configured to control distraction of the first blade in response to pivotal motion of the first handle, a second handle pivotally coupled to the body, a second attachment assembly comprising a second button configured to allow detachment of a fourth handle portion from the second handle, a second arm assembly attached to the second handle, and a second blade attached to the second arm assembly, wherein the second handle is configured to control distraction of the second blade in response to pivotal motion of the second handle.

10 Claims, 13 Drawing Sheets

(56) References Cited

U.S. PATENT DOCUMENTS

| | | |
|---|---|---|
| 9,693,762 B2 | 7/2017 | Reimels |
| 9,848,863 B2 | 12/2017 | Cryder et al. |
| 9,861,273 B2 | 1/2018 | Weiman |
| 10,039,539 B2 | 8/2018 | Friedrich et al. |
| 10,130,348 B2 | 11/2018 | Cryder et al. |
| 10,154,781 B2 | 12/2018 | Weiman |
| 10,285,680 B2 | 5/2019 | Friedrich et al. |
| 10,463,354 B2 | 11/2019 | Friedrich et al. |
| 10,478,169 B2 | 11/2019 | Cianfrani et al. |
| 10,709,434 B2 | 7/2020 | Friedrich et al. |
| 10,874,387 B2 | 12/2020 | Karpowicz et al. |
| 2012/0283521 A1* | 11/2012 | Smith ................ A61B 17/0206 600/210 |
| 2012/0296171 A1* | 11/2012 | Lovell ................ A61B 17/0218 600/213 |
| 2013/0158359 A1* | 6/2013 | Predick .............. A61B 17/0206 600/224 |
| 2015/0250466 A1* | 9/2015 | Thornburg .......... A61B 17/0206 600/224 |
| 2016/0051242 A1* | 2/2016 | Predick .............. A61B 17/0206 600/224 |
| 2016/0317137 A1* | 11/2016 | Predick .............. A61B 17/0206 |
| 2016/0361052 A1* | 12/2016 | Reimels ............. A61B 17/0206 |
| 2018/0085105 A1* | 3/2018 | Kim ................... A61B 17/0206 |

* cited by examiner

ORTHOPEDIC RETRACTOR

CROSS-REFERENCE TO RELATED APPLICATIONS

This application is a continuation of U.S. application Ser. No. 16/351,298 filed Mar. 12, 2019, which claims the benefit of and/or priority under 35 U.S.C. § 119(e) to U.S. provisional application Ser. No. 62/641,782 filed Mar. 12, 2018, all of which are incorporated herein by reference.

FIELD

The present invention relates to retractors used in orthopedic surgery and, more particularly, to retractors used for lateral spine surgery.

BACKGROUND

Many surgical procedures necessitate the use of a medical device known as a surgical retractor. A surgical retractor is used to separate the edges of a surgicalincision or wound, or to hold back underlying organs and tissues so that body parts under the incision may be accessed. A wide variety of retractors are used for various types of surgical procedures such as orthopedic surgery, cosmetic surgery, cardiothoracic surgery, gastrointestinal surgery, gynecological surgery, urological surgery, and others. Surgical retractors are thus uniquely designed for different functions.

Within the category of orthopedic surgery there are various types of retractors depending on whether the procedure involves the leg, hip, arm, shoulder, or spine. There are even variations in retractors within the category of orthopedic spine surgery depending on whether the procedure involves the lumbar, cervical, thoracic, or sacrum portion of the spine. Orthopedic retractors for the spine are even further differentiated by whether the spine surgery is an anterior approach or procedure, a posterior approach or procedure, or a lateral approach or procedure.

One type of spine surgery that utilizes a lateral approach or procedure is vertebral fusion. In vertebral fusion the vertebral disc between adjacent vertebrae is removed or supplemented with an implant known as a cage or interbody device. A retractor is used to hold the incision and/or the adjacent vertebrae in order to remove the disc and/or install the implant. It may also be used for other purposes during the spinal procedure.

Orthopedic retractors for spine surgery typically use blades that can be manipulated in order to perform various functions. It is thus desirable for the blades of the orthopedic retractor to be easily manipulated by the surgeon. It is also desirable that the retractor allow the blades to be moved in various directions and/or placed in various positions. It is also desirable that the retractor allow the blades to be manipulated into particular orientations. Prior art orthopedic retractors for lateral spine surgery are currently deficient in these abilities.

It is therefore an object of the present invention to provide an orthopedic retractor for lateral spine surgery that overcomes the deficiencies of the prior art. It is also an object of the present invention to provide an orthopedic retractor that incorporates one or more of the above desires.

The aforementioned and other objects and desires are satisfied by the present orthopedic retractor for lateral spine surgery.

SUMMARY

An orthopedic retractor provides lateral access to the lumbar portion of the spine utilizing a minimally invasive technique by distracting (drawing apart) soft tissue and psoas muscle leading up to the lumbar disc for a spinal fusion procedure by position controllable blades. The orthopedic retractor provides linear distraction of its blades as well as blade angulation in order to minimize the amount of tissue disruption and maximize exposure of the lumbar disc space.

The orthopedic retractor has two lateral blades and one medial blade. Each lateral blade is attached to a lateral blade arm/arm assembly that is attached to a handle for controlling distraction. The medial blade is attached to a medial arm/arm assembly that is attached to a medial drive assembly for controlling its distraction. The medial drive assembly has a threaded rod that is attached at one end to the medial arm assembly and at another end to a medial knob wherein rotation thereof controls distraction of the medial blade. Opening and closing of the handles draws apart (distracts) and draws close (retracts) the lateral blades. Rotation of the medial knob in one direction distracts the medial blade while rotation of the middle knob in an opposite direction retracts the medial blade.

Proximal portions of the handles may be detached for easier access to the medial knob.

A distraction control assembly is associated with each handle and provides precise and individual adjustment of handle position for precise and individual distraction and retraction of the lateral blade associated with the particular handle. Each distraction control assembly includes a spring loaded threaded expansion knob extending through the handle and threadedly received in the body.

Angulation assemblies are associated with each of the two lateral arm assemblies and the medial arm assembly, and are used to individually angulate the lateral blades and the medial blade for maximum exposure. The angulation assemblies provide individual control of the angle or tilt of each blade.

In one form, each angulation assembly consists of a threaded angulation knob that threads into a distal arm of a blade holder assembly and a spherical ball that is seated in a spherical pocket in a mating proximal arm of the blade holder assembly. The threaded angulation knob is received by the spherical ball. When torque is applied to the spherical ball by the threaded angulation knob, it will cause the distal arm to tilt or angulate relative to the proximal arm. Each distal arm holds a blade assembly having a blade.

The blade assembly consists of a blade holder and a blade. The blade holder is configured for reception in an associated distal arm of the blade holder assembly—i.e. a first lateral distal arm for the first lateral blade, a second lateral distal arm for the second lateral blade, and a medial distal arm for the medial blade. The first lateral distal arm is connected to the first lateral proximal arm of the blade holder assembly, the second lateral distal arm is connected to the second lateral proximal arm of the blade holder assembly, and the medial distal arm is connected to the medial proximal arm.

Each blade assembly includes a blade lock that is inserted into the distal arm and threaded into the blade. The blade lock has a landing that sits on top of the arm and retains the blade in the arm house. There is also a c-clip that prevents the blade lock from coming out after the blade is removed.

The orthopedic retractor is preferably, but not necessarily, made from a combination of surgical grade stainless steel, titanium, and plastic.

BRIEF DESCRIPTION OF THE DRAWING FIGURES

The above mentioned and other features and objects of this invention, and the manner of attaining them, will become more apparent and the invention itself will be better understood by reference to the following description of a form of the invention taken in conjunction with the accompanying drawings, wherein.

A detailed description of the features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION

Figure 25:
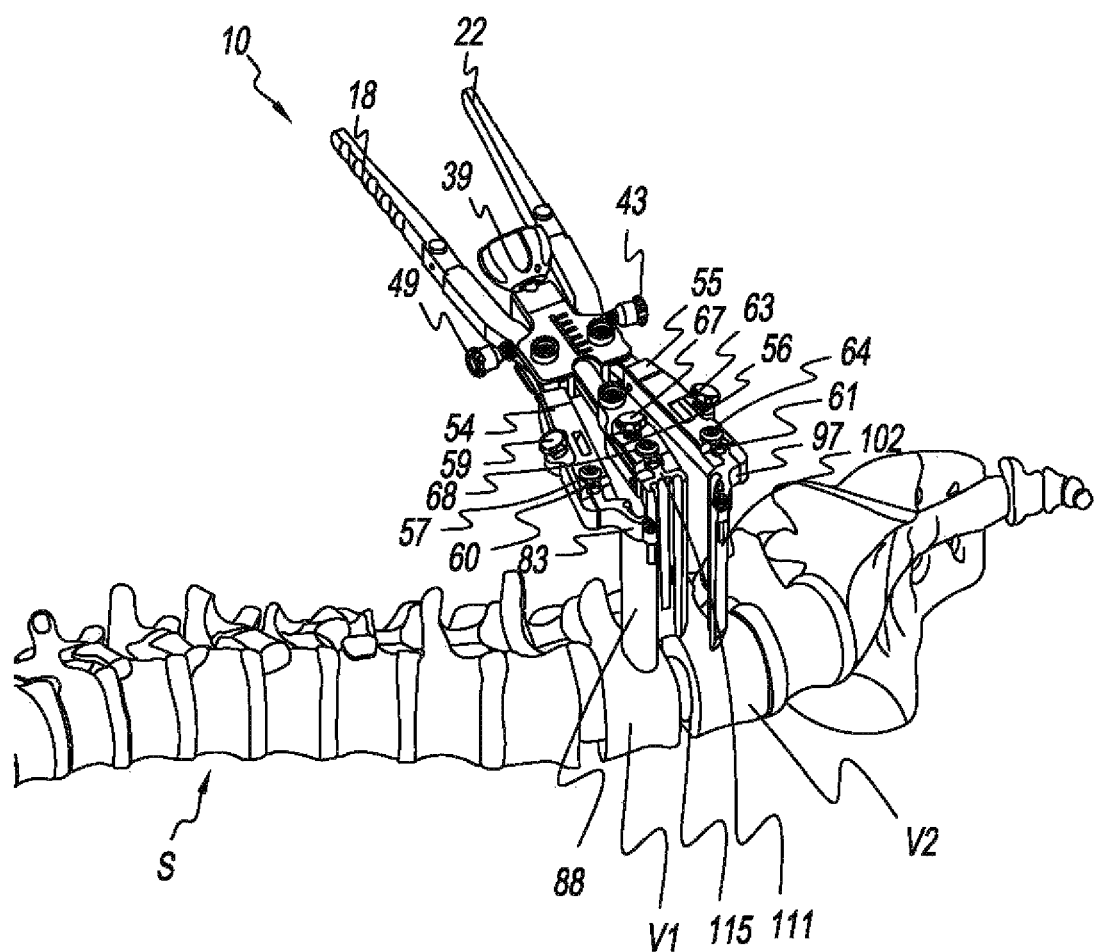
FIG. 25 is an isometric view of the orthopedic retractor of FIG. 1 ready to perform a lateral spine procedure on the lumbar portion of the spine.

FIGS. 1-24 depict various views of an orthopedic retractor, generally designated 10, and/or its constituent components fashioned in accordance with the present principles, for use in lateral spine surgery/surgical procedures as exemplified in the illustration of FIG. 25, and with and without retractor blades, distracted or not distracted, and with some of the retractor blades angulated. Reference is thus made to the Description of the Drawing Figures. The orthopedic retractor, spine retractor, or lateral spine retractor 10 is preferably, but not necessarily, fashioned from various surgical grade materials such as stainless steel, titanium, and plastic, the plastic preferably, but not necessarily, being a polyphenylsulfone (PPSU), a sulfone polymer. Such a PPSU may be Radel® made by Aetna Plastics Corp of Valley View Ohio, US. Other surgical grade materials may be used. The lateral retractor 10 is used to provide lateral access to the spine and preferably, but not necessarily, the lumbar portion of the spine as illustrated in FIG. 25. The orthopedic retractor 10 is preferably, but not necessarily, used for a minimally invasive technique by distracting the soft tissue and psoas muscle leading up to the lumbar disc for spinal fusion. The retractor allows for linear distraction as well as blade angulation to minimize the amount of tissue disruption and for maximum exposure to the lumbar disc space. Other spinal surgical procedures are contemplated. It should be appreciated that the nomenclature first and second used herein is arbitrary, as is upper and lower, unless specifically indicated otherwise.

As best seen in FIGS. 3-6, the orthopedic retractor 10 has a generally rectangular body 12 defining a box-like neck 26 with a first upper flange 27 formed generally on a first lateral side, a first lower flange 28 formed generally on the first lateral side but axially below the first upper flange 27, a second upper flange 32 formed generally on a second lateral side opposite the first lateral side, and a second lower flange 33 formed generally on the second lateral side but axially below the second upper flange 28. A cavity 29 is defined between the first upper flange 27and the first lower flange 28. A post 30 is disposed at a distal end of the cavity 29 between the lower surface of the first upper flange 27 and the upper surface of the first lower flange 28. The cavity 29 receives a distal or lower portion 23 of a second handle 15 while the post 30 pivotally retains the distal portion 23 of the second handle 15. A cavity 34 is defined between the second upper flange 32 and the second lower flange 33. A post 35 is disposed at the distal end of the cavity 34 between the lower surface of the second upper flange 32 and the upper surface of the second lower flange 33. The cavity 34 receives a distal or lower portion 19 of a first handle 14 while the post 35 pivotally retains the distal portion 19 of the first handle 14.

Figure 1:
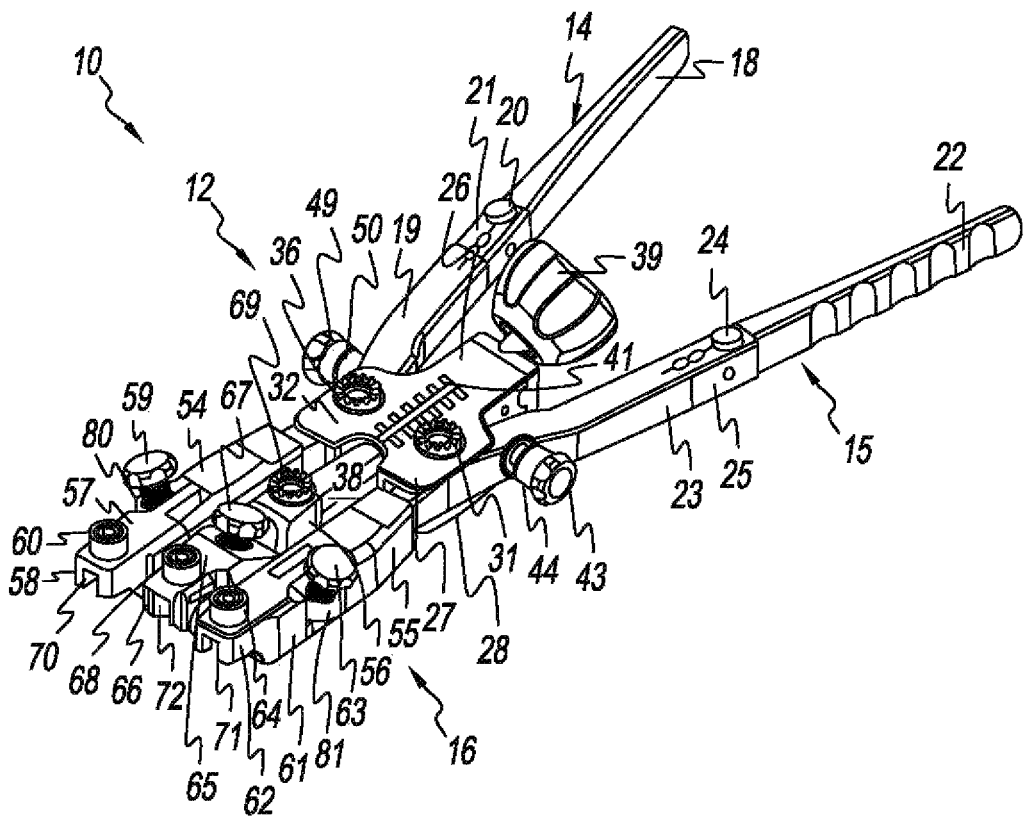
FIG. 1 is an isometric upper view of an orthopedic retractor for lateral spine surgery fashioned in accordance with the present principles, the orthopedic retractor shown without retractor blades and in a non-distracted state.
Figure 2:
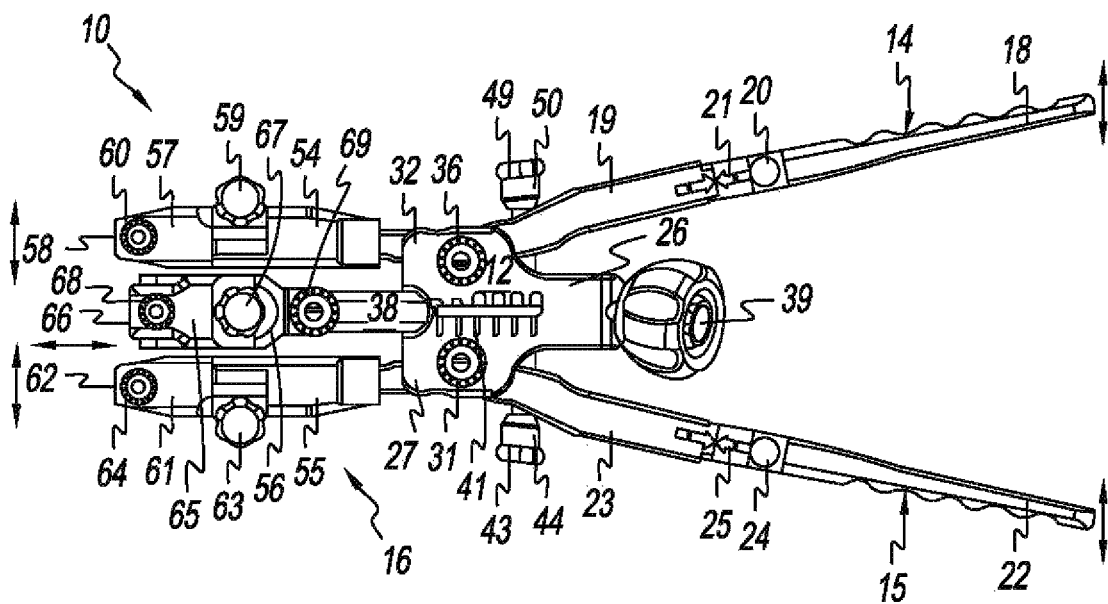
FIG. 2 is a top plan view of the orthopedic retractor of FIG. 1 without retractor blades and in a non-distracted state.
Figure 3:
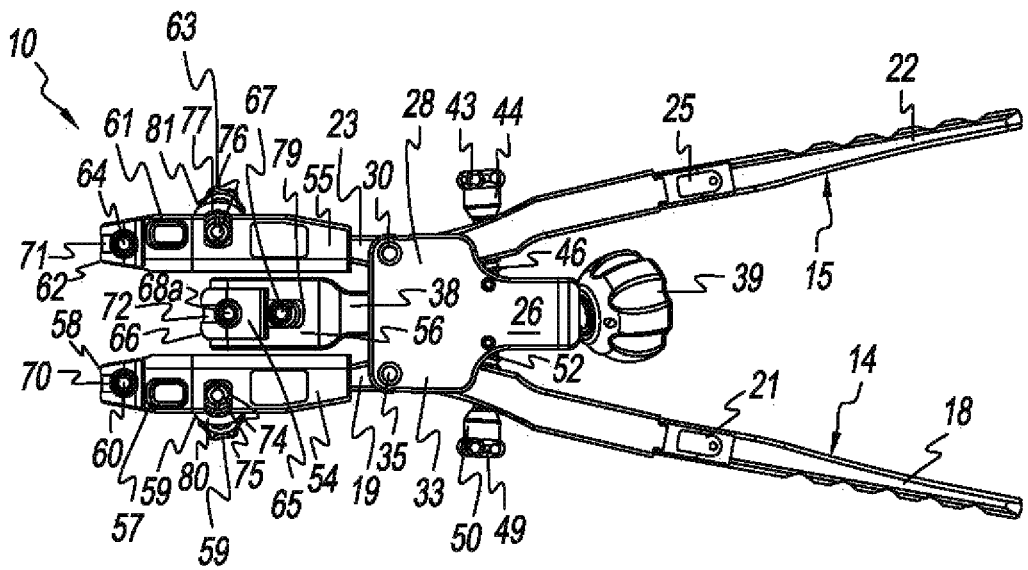
FIG. 3 is a bottom plan view a bottom plan view of the orthopedic retractor of FIG. 1 without retractor blades and in a non-distracted state.
Figure 4:
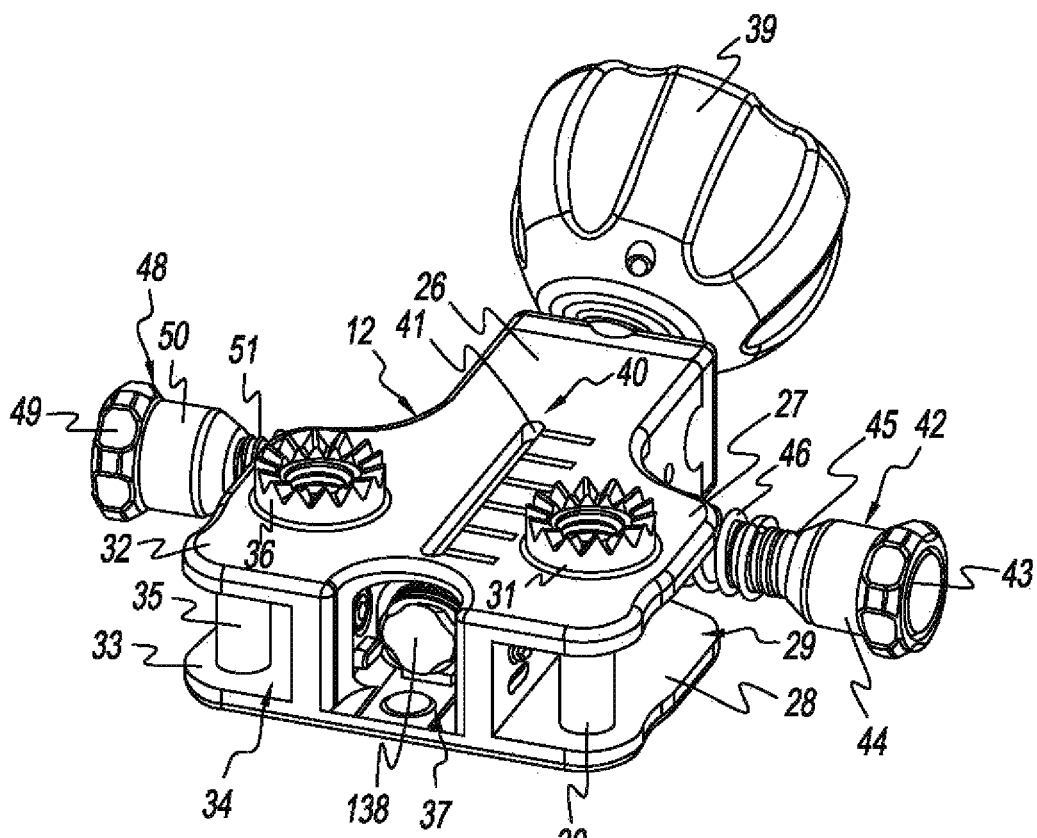
FIG. 4 is an enlarged isometric upper view of a body of the orthopedic retractor of FIG. 1 without its blade holder assembly or handles.
Figure 5:
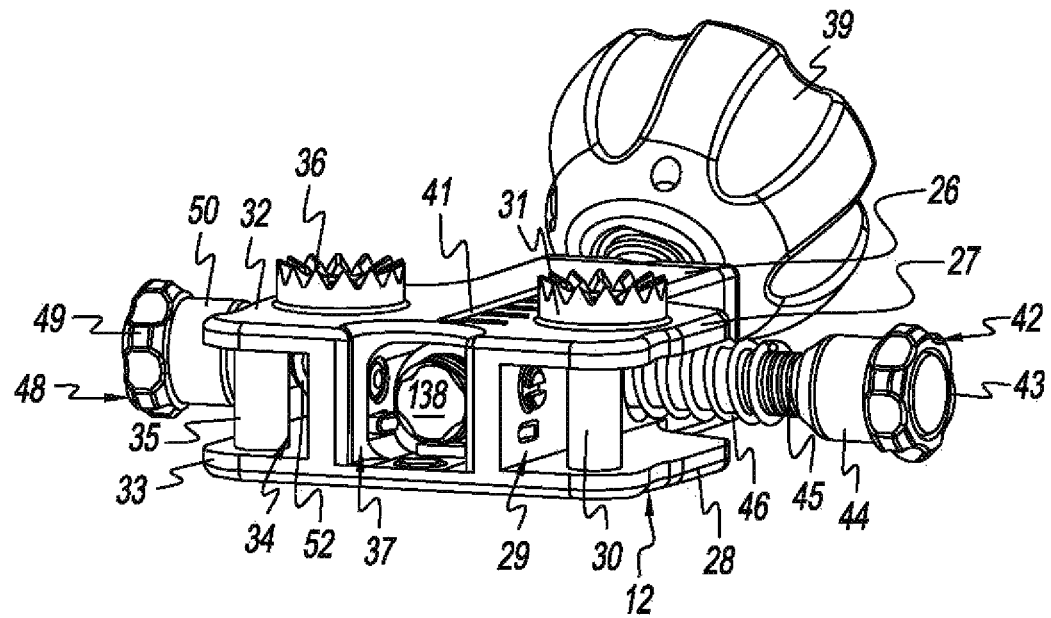
FIG. 5 is another enlarged isometric upper view of the body of FIG. 4 without its blade holder assembly or handles.
Figure 6:
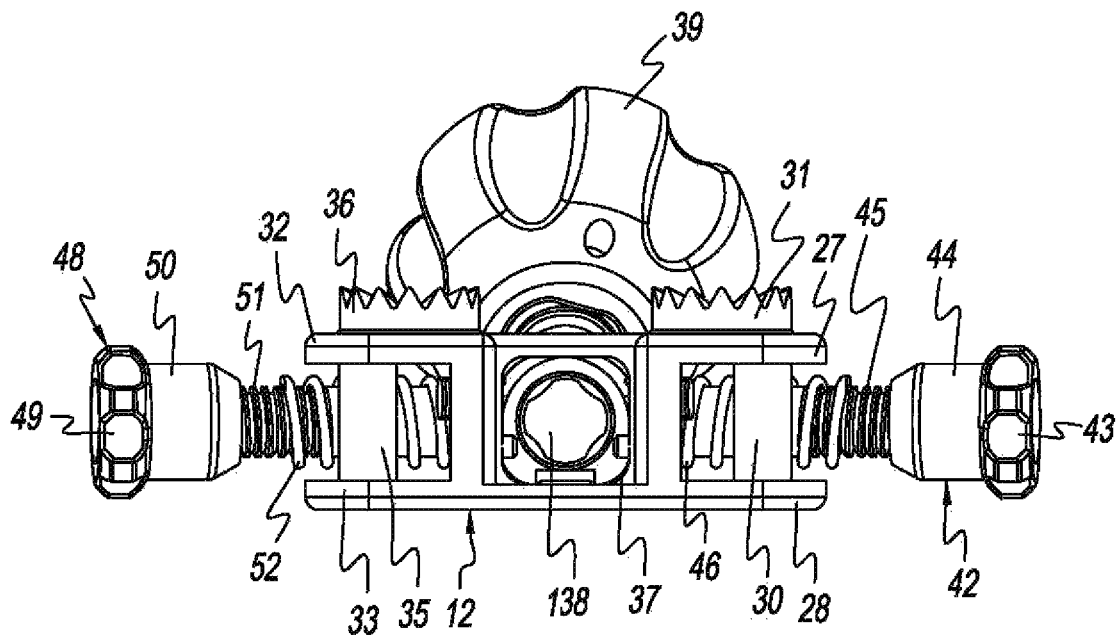
FIG. 6 is an enlarged front view of the body of FIG. 4 without its blade holder assembly or handles.

As best seen in FIGS. 1-3, the first handle 14 is formed by a proximal or upper handle portion 18 and a distal or lower handle portion 19. The upper handle portion 18 is detachably joined to the lower handle portion 19 by a connector or attachment mechanism 21. A button 20 or the like allows release of the upper handle portion from the lower handle portion via the connector/attachment mechanism 21. The lower handle portion 19 is pivotally coupled to the body 12 via the pivot post 30. The lower handle portion 19 has a distal end that is curved outwardly relative to a proximal end thereof and to the upper handle portion 18. Inward movement of the upper handle portion 18 pivots the lower handle portion18 outward (distraction). Outward movement of the upper handle portion 18 pivots the lower handle portion 18 inward (retraction). Overall, inward movement of the first handle 14 produces distraction while outward movement of the first handle 14 produces retraction. As developed more fully below, the lower handle portion 19 is connected to a first lateral arm assembly consisting of a first lateral proximal or upper arm 54 and a first lateral distal or lower arm 57 of a blade holder assembly 16 which holds a first lateral blade 88. The first handle 14 thus provides distraction and retraction of the first lateral blade 88.

The second handle 15 is formed by a proximal or upper handle portion 22 and a distal or lower handle portion 23. The upper handle portion 22 is detachably joined to the lower handle portion 23 by a connector or attachment mechanism 25. A button 24 or the like allows release of the upper handle portion from the lower handle portion via the connector/attachment mechanism 25. The lower handle portion 23 is pivotally coupled to the body 12 via the pivot post 35. The lower handle portion 23 has a distal end that is curved outwardly relative to a proximal end thereof and to the upper handle portion 22. Inward movement of the upper handle portion 22 pivots the lower handle portion 23 outward (distraction). Outward movement of the upper handle portion 22 pivots the lower handle portion 23 inward (retraction). Overall, inward movement of the second handle 15 produces distraction while outward movement of the second handle 15 produces retraction. As developed more fully below, the lower handle portion 23is connected to a second lateral arm assembly consisting of a second lateral proximal or upper arm 55 and a second lateral distal or lower arm 61 of the blade holder assembly 16 which holds a second lateral blade 102. The second handle 15 thus provides distraction and retraction of the second lateral blade 102.

The body 12 carries a medial drive assembly 37 having a threaded screw 138that extends from the distal end of the body 12 to the proximal end of the body 12. A medial knob 39 is attached to the proximal end of the threaded screw 138. Rotation of the medial knob 39 rotates the threaded screw 138. The medial knob39 allows rotation in the clockwise and counter-clockwise directions which rotates the threaded screw 138 in the clockwise and counter-clockwise directions. The medial drive assembly 37 controls distraction of a medial blade 115 as further explained below. A gauge 40 is provided on the body 12 for indicating amount of medial blade distraction. The gauge 40 includes a slot 41 that allows viewing of the threaded screw 138 such that a mark, marker or otherwise on the threaded screw 138 can be seen within the slot 41. Side demarcations are provided on the body adjacent the slot 41. Movement of the threaded screw 138 moves the mark/marker along the side demarcations.

A first serrated nut 31 is disposed on the upper surface of the first upper flange 27 while a second serrated nut 36 is disposed on the upper surface of the second upper flange 32. The serrated nuts 31, 35 are configured for fixation to a table arm (not shown) that is mounted on a table (not shown) that the patient is lying on for the surgical procedure. The table arm can be manipulated into any position and then fixed rigidly so the retractor does not move (except for blade distraction and angulation) during the surgery. A further serrated nut 69 for table arm fixation may be provided on a medial proximal arm 56 of a medial arm assembly comprising the medial proximal arm 56 and a medial distal arm 65.

The body 12 also includes a first distraction control assembly 42 that provides precise distraction and retraction of the first lateral blade 88. The first distraction control assembly 42 provides fine-tuning adjustment of distraction/retraction of the first lateral blade 88. The first distraction control assembly 42 includes a bolt43 having a neck 44 that narrows to a threaded shaft 45. The threaded shaft 45 extends through a bore in the lower or distal handle portion 19 of the first handle 14 and is threadedly received by the body 12. A spring 46 is provided on the threaded shaft 45 between the lower or distal handle portion 19 and the body 12 to bias the first handle 14 outwardly. Rotation of the bolt 43 in one direction pushes the first handle 14 inwardly for distraction of the first lateral blade 88, while rotation of the bolt 43 in the opposite direction allows the spring 46 to bias the first handle 14 outwardly for retraction of the first lateral blade 88.

The body 12 further includes a second distraction control assembly 48 that provides precise distraction and retraction of the second lateral blade 102. The second distraction control assembly 48 provides fine-tuning adjustment of distraction/retraction of the second lateral blade 102. The second distraction control assembly 48 includes a bolt 49 having a neck 50 that narrows to a threaded shaft 51. The threaded shaft 51 extends through a bore in the lower or distal handle portion 23 of the second handle 15 and is threadedly received by the body 12. A spring 52 is provided on the threaded shaft 51 between the lower or distal handle portion 23 and the body 12 to bias the second handle 15 outwardly. Rotation of the bolt 49 in one direction pushes the second handle 15inwardly for distraction of the second lateral blade 102, while rotation of the bolt 49 in the opposite direction allows the spring 52 to bias the second handle 15 outwardly for retraction of the second lateral blade 102.

In addition to the first lateral arm assembly consisting of the first lateral proximalor upper arm 54 and the first lateral distal or lower arm 57 which holds the first lateral blade 88, and the second lateral arm assembly consisting of the second lateral proximal or upper arm 55 and the second lateral distal or lower arm 61 which holds the second lateral blade 102, the blade holder assembly 16 has a medial arm assembly consisting of a medial proximal or upper arm 56 and a medial distal or lower arm 65 which hold a medial blade 115. The medial arm assembly provides distraction and retraction of the medial blade 115.

Figure 7:
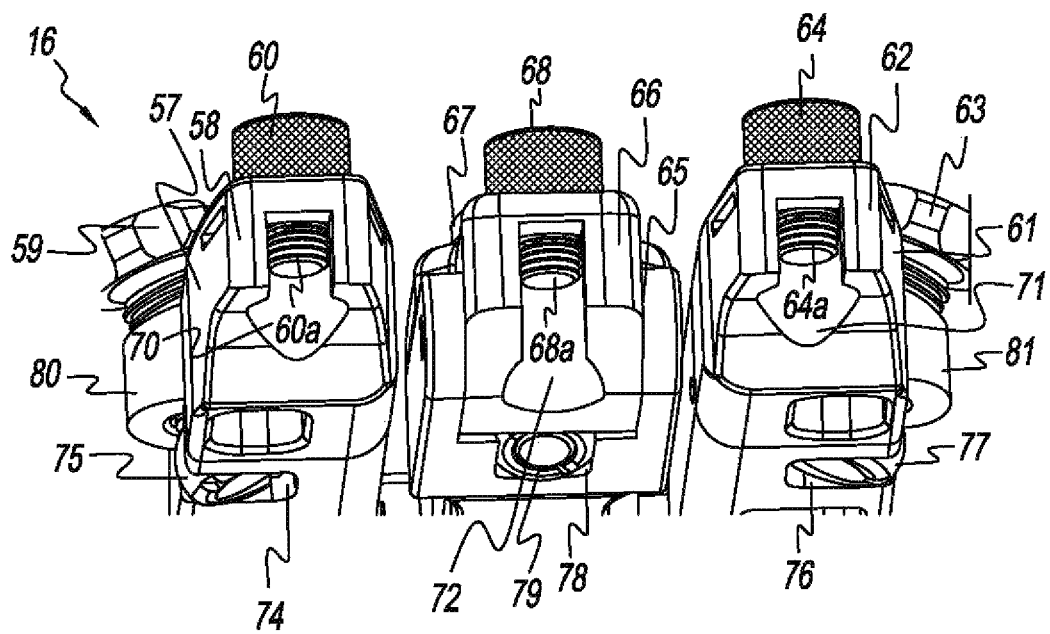
FIG. 7 is an enlarged isometric front view of the distal arms of the blade holder assembly of the orthopedic retractor of FIG. 1 without blades.
Figure 8:
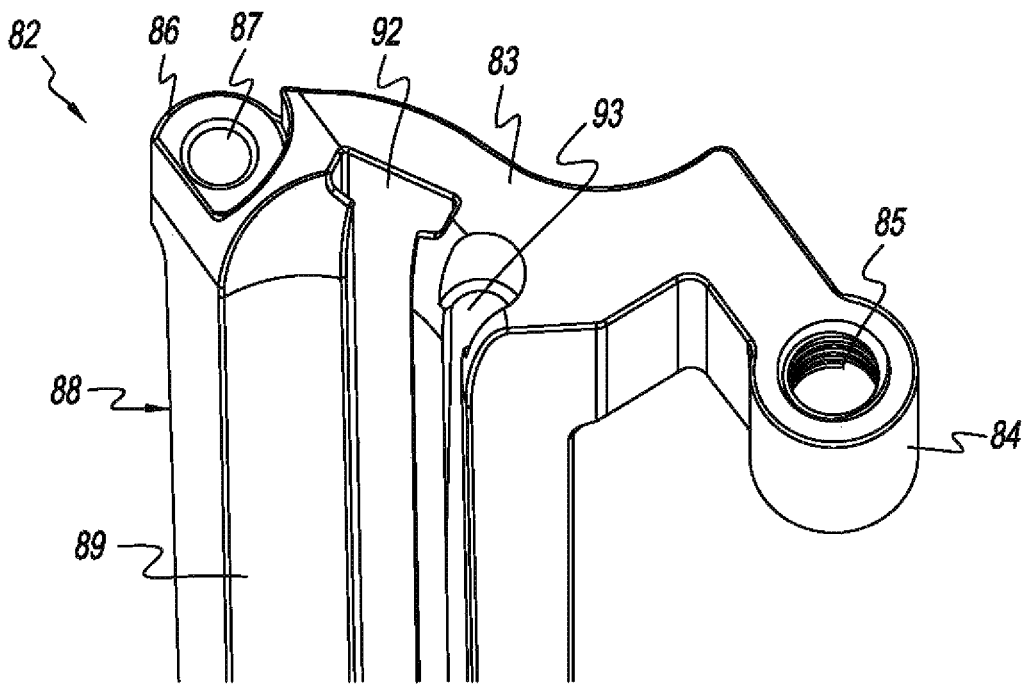
FIG. 8 is an enlarged isometric top view of an upper portion of a blade assembly of the orthopedic retractor of FIG. 1.
Figure 9:
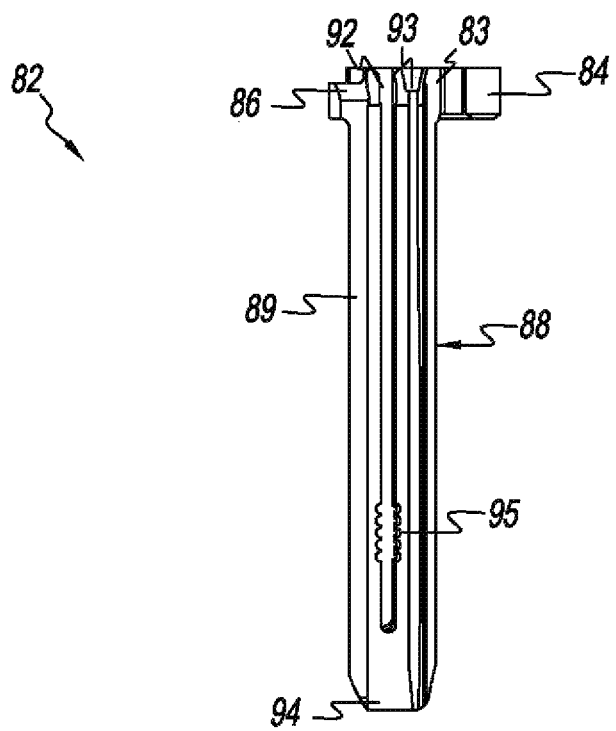
FIG. 9 is a proximal plan view of a blade assembly of the orthopedic retractor of FIG. 1.
Figure 10:
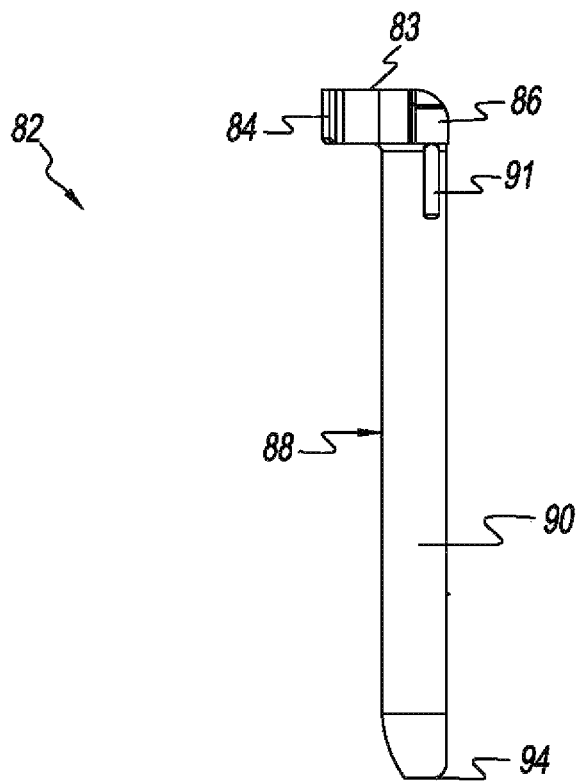
FIG. 10 is a lateral plan view the blade assembly of FIG. 9.
Figure 11:
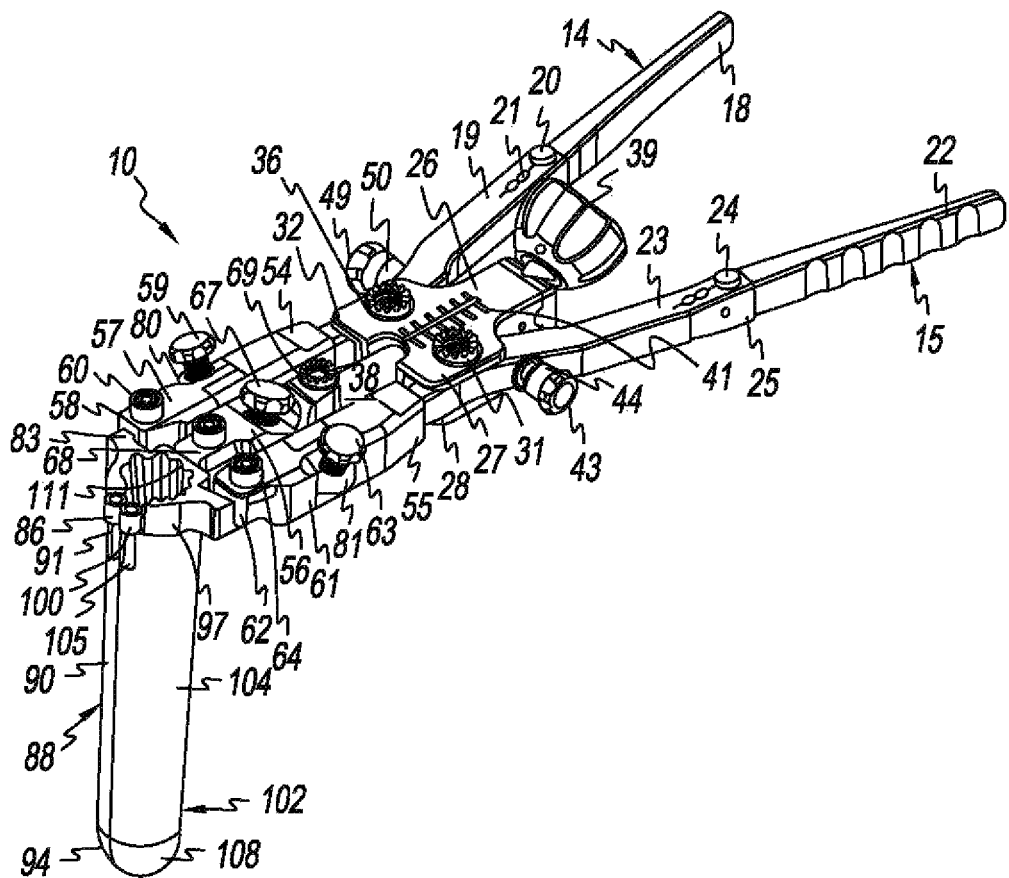
FIG. 11 is an isometric upper view of the orthopedic retractor of FIG. 1 shown with retractor blades and in a non-distracted state.
Figure 12:
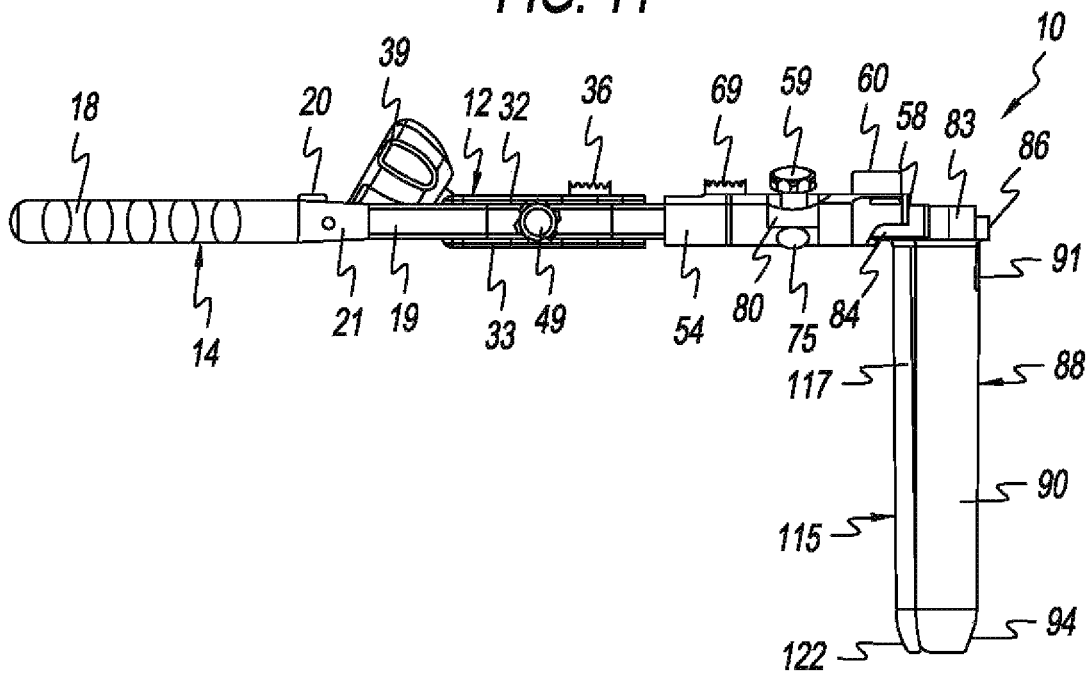
FIG. 12 is a side view of the orthopedic retractor of FIG. 11.
Figure 13:
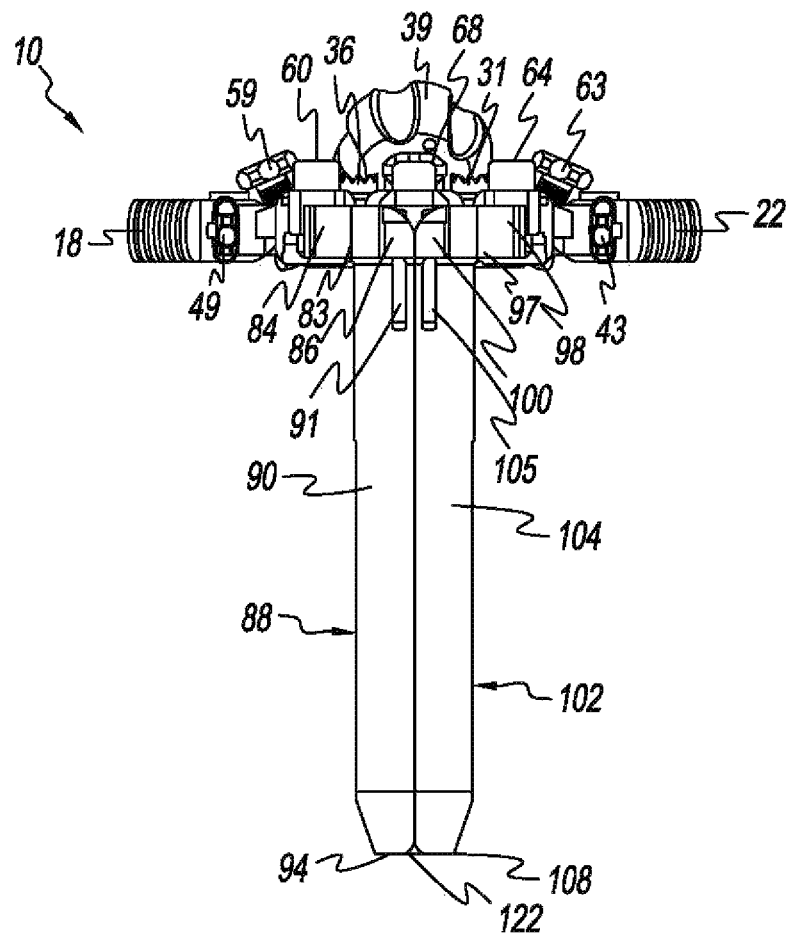
FIG. 13 is a front view of the orthopedic retractor of FIG. 11.
Figure 14:
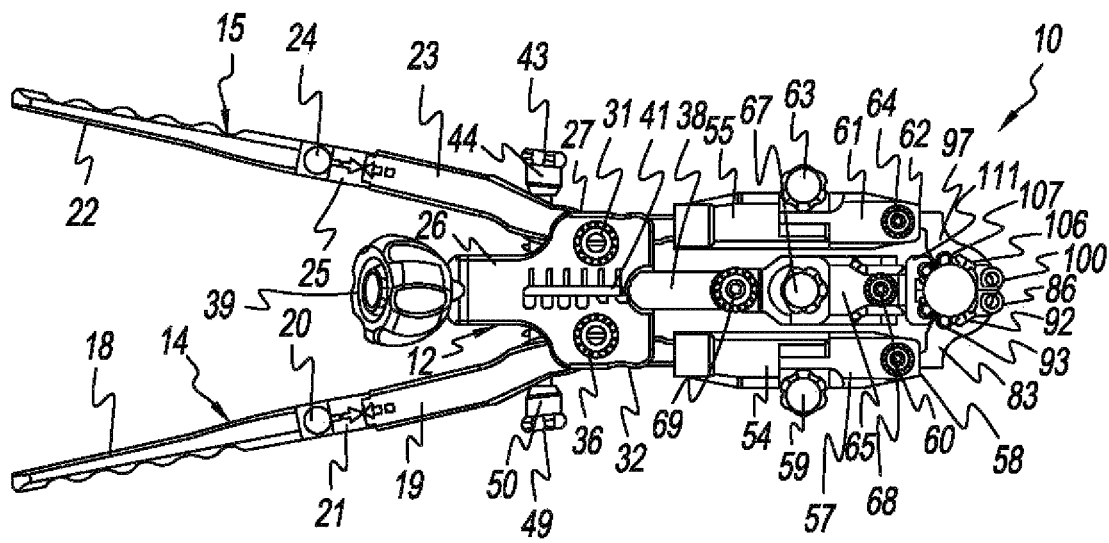
FIG. 14 is a top plan view of the orthopedic retractor of FIG. 1 shown with retractor blades and in a non-distracted state.
Figure 15:
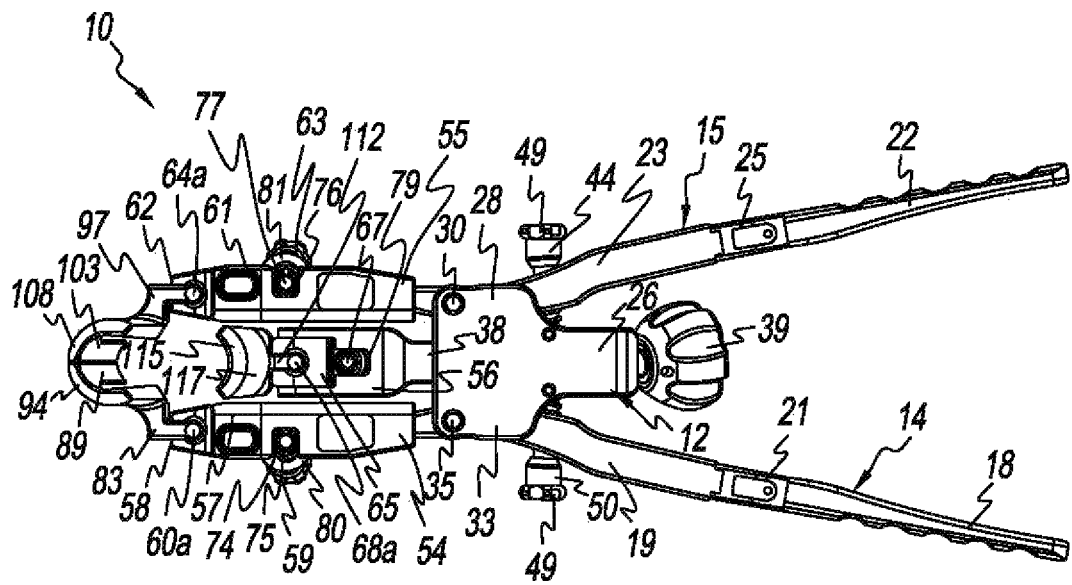
FIG. 15 is a bottom plan view of the orthopedic retractor of FIG. 1 shown with retractor blades and in a non-distracted state.
Figure 16:
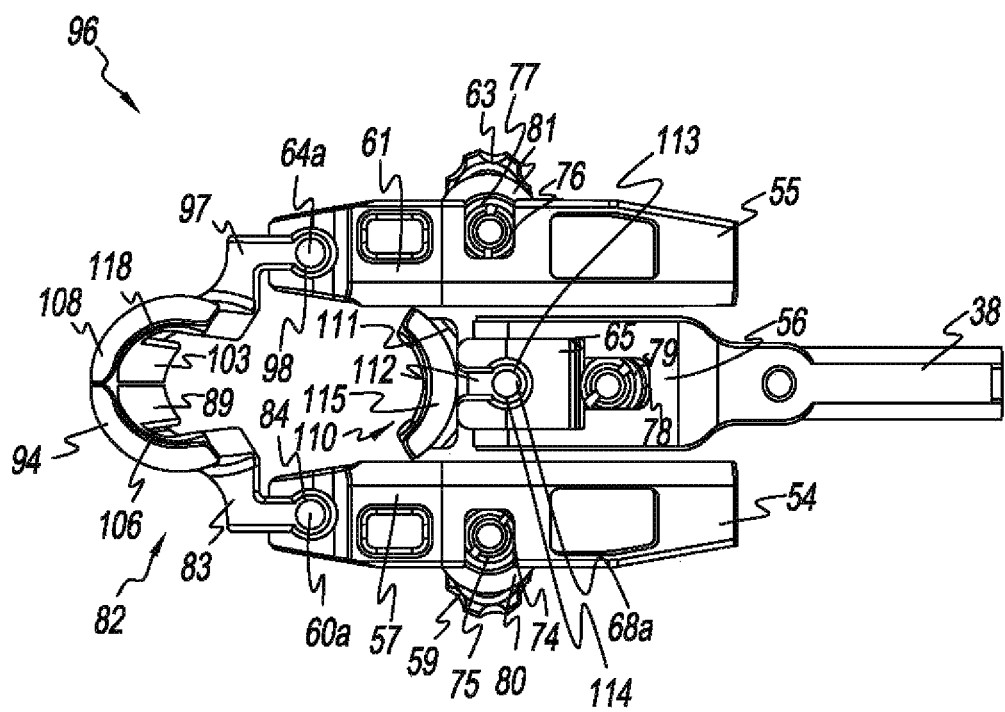
FIG. 16 is an enlarged bottom plan view of the blade holder assembly of the orthopedic retractor of FIG. 1.
Figure 17:
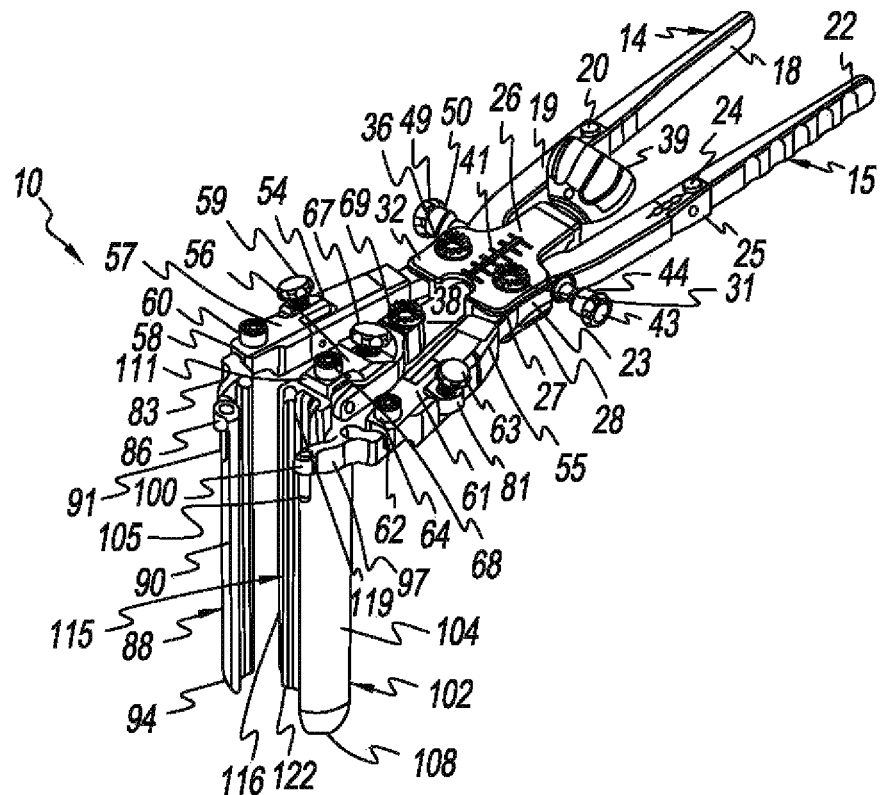
FIG. 17 is an isometric upper view of the orthopedic retractor of FIG. 1 shown with retractor blades and in a distracted state.
Figure 18:
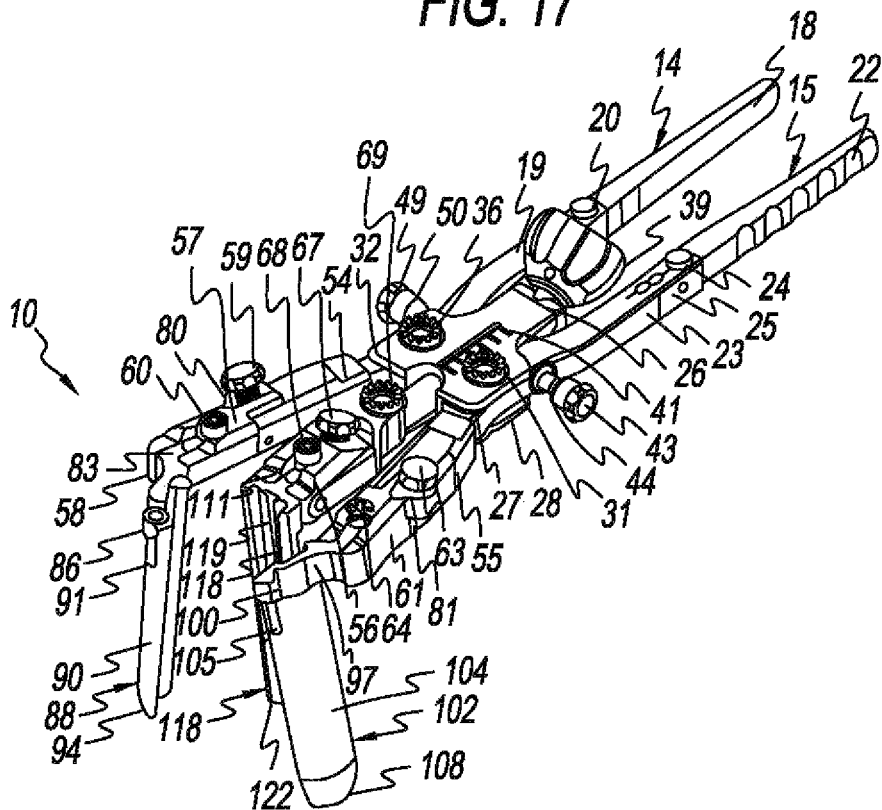
FIG. 18 is an isometric upper view of the orthopedic retractor of FIG. 1 shown with retractor blade and in a distracted state with an angulated lateral blade.

As best seen in FIGS. 20-24, as well as FIG. 7, the first lateral proximal arm 54 is connected at one end to the distal or lower end of the lower handle portion 19 of the first handle 14. The other end of the first lateral proximal arm 54 is pivotally connected to one end of the first lateral distal arm 57. The other end of the first lateral distal arm 57 terminates in an end 58 configured to receive a first lateral blade assembly 82 which holds the first lateral blade 88. The first lateral distal arm 57 pivots, angulates or tilts relative to the first lateral proximal arm 54 which, in turn, pivots, angulates or tilts the first lateral blade assembly 82 and thus the first lateral blade 88. In this manner, the first lateral blade 88 can angulate relative to the first lateral proximal arm 54 and thus the body 12. Angulation is controlled and adjusted by a first angulation assembly consisting of a first spherical pocket 74 in the first lateral proximal arm 54, a first spherical ball 75 situated in the first spherical pocket 74, and a first threaded angulation bolt 59 threadedly received in a first boss 80 of the first lateral proximal arm 54. The first angulation bolt 59 is received by the first spherical ball 75. Rotation of the first angulation bolt 59 produces or releases torque against the first spherical ball 75 which, in turn, causes the first lateral distal arm 57 to pivot in one direction or in an opposite direction, thereby providing controlled and adjustable angulation of the first blade holder assembly 82 and thus the first lateral blade 88 retained thereby.

The second lateral proximal arm 55 is connected at one end to the distal or lower end of the lower handle portion 23 of the second handle 15. The other end of the second lateral proximal arm 55 is pivotally connected to one end of the second lateral distal arm 61. The other end of the second lateral distal arm 61 terminates in an end 62 configured to receive a second lateral blade assembly 96 which holds the second lateral blade 102. The second lateral distal arm 61 pivots, angulates or tilts relative to the second lateral proximal arm 55 which, in turn, pivots, angulates or tilts the second lateral blade assembly 96 and thus the second lateral blade 102. In this manner, the second lateral blade 102 can angulate relative to the second lateral proximal arm 55 and thus the body 12.

Angulation is controlled and adjusted by a second angulation assembly consisting of a second spherical pocket 76 in the second lateral proximal arm 55, a second spherical ball 77 situated in the second spherical pocket 76, and a second threaded angulation bolt 63 threadedly received in a second boss 81 of the second lateral proximal arm 55. The second angulation bolt 63 is received by the second spherical ball 77. Rotation of the first angulation bolt 63 produces or releases torque against the second spherical ball 77 which, in turn, causes the second lateral distal arm 61 to pivot in one direction or in an opposite direction, thereby providing controlled and adjustable angulation of the second blade holder assembly 96 and thus the second lateral blade 102 retained thereby.

The medial proximal arm 56 is connected at one end to a connection member 38 which in turn, is threadedly connected to the drive shaft 138 of the drive assembly 37. The drive assembly 37 controls medial distraction and retraction of the medial arm assembly and thus the medial blade 115 through rotation of the medial drive knob 39. The other end of the medial proximal arm 56 is pivotally connected to one end of the medial distal arm 65. The other end of the medial distal arm 65 terminates in an end 66 configured to receive a medial blade assembly 110 which holds the medial blade 115. The medial distal arm 65 pivots, angulates or tilts relative to the medial proximal arm 56 which, in turn, pivots, angulates or tilts the medial blade assembly 110 and thus the medial blade 115. In this manner, the medial blade 115 can angulate relative to the medial proximal arm 56 and thus the body 12. Angulation is controlled and adjusted by a medial angulation assembly consisting of a medial spherical pocket 78 in the medial proximal arm 56, a medial spherical ball 79 situated in the medial spherical pocket 78, and a medial angulation bolt 67 threadedly received in the medial proximal arm 56. The medial angulation bolt 67 is received by the medial spherical ball 79. Rotation of the medial angulation bolt 67 produces or releases torque against the medial spherical ball 79 which, in turn, causes the medial distal arm 65 to pivot in one direction or in an opposite direction, thereby providing controlled and adjustable angulation of the medial blade holder assembly 110 and thus the medial blade 115 retained thereby. Angulation of various of the blades is illustrated in FIGS. 17-20.

Figure 23:
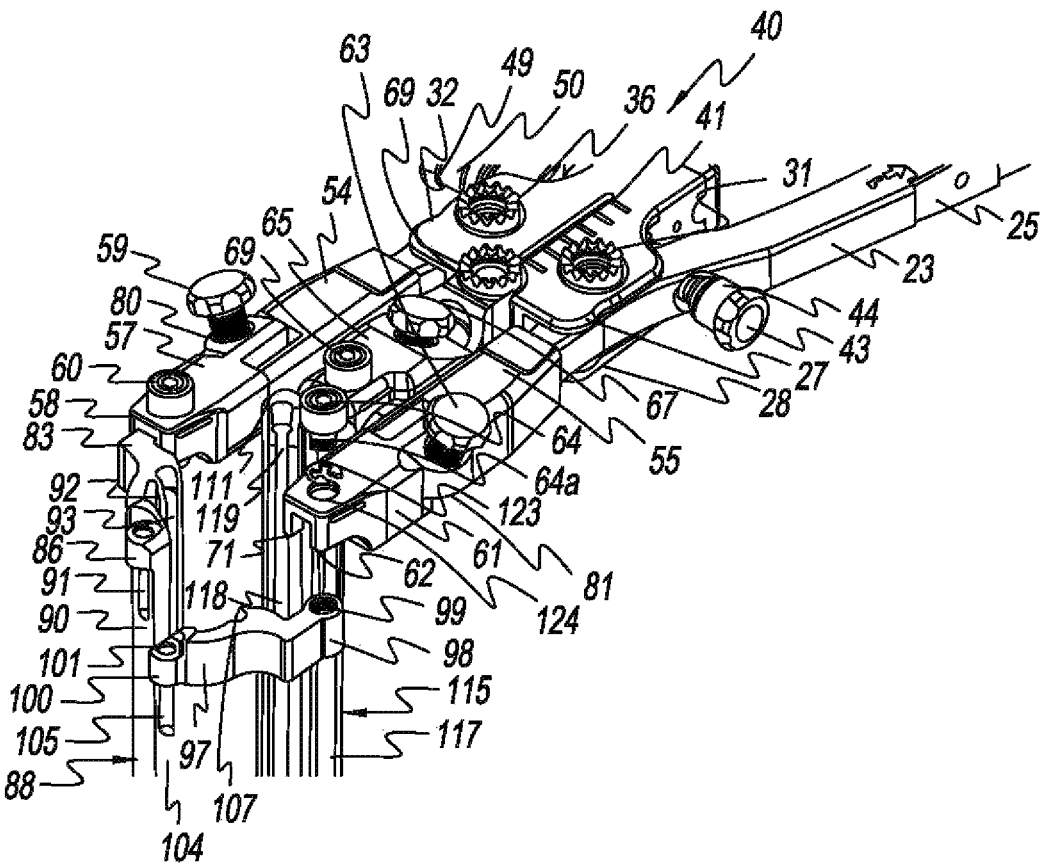
FIG. 23 is an enlarged isometric upper of the blade holder assembly of the orthopedic retractor of FIG. 1 illustrating how a blade assembly is received by the blade holder assembly.
Figure 24:
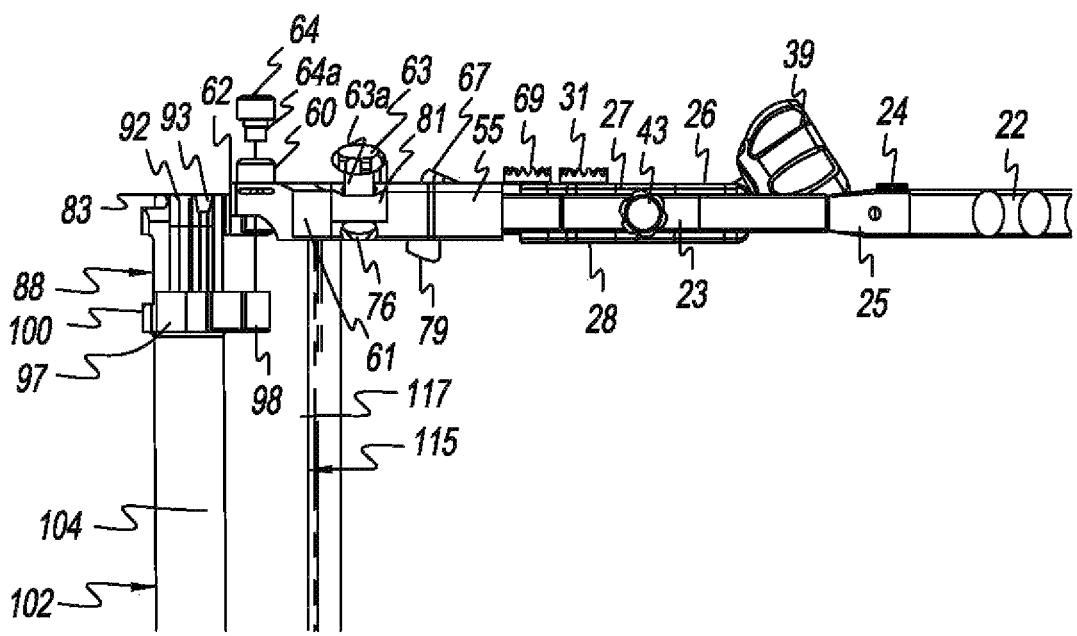
FIG. 24 is a side plan view of the orthopedic retractor depicted in FIG. 23.

As seen best in FIGS. 8-10 and 23-24, the first lateral blade holder assembly 82 includes a first lateral blade holder 83 and the first lateral blade 88 that extends from the first lateral blade holder 83. The first lateral blade holder 83 is configured as an elongated arm and includes a generally round boss 84 at one end having a threaded bore 85 extending therethrough, and a configured end 86 at another end opposite the boss 84 and having a bore 87 therethrough. The first lateral blade holder 83 is configured to be received in a like-configured notch 70 disposed in the underside of the distal end 58 of the first lateral distal arm 57. The threaded bore 85 receives a threaded shaft 60a of a first lateral blade lock bolt 60 extending through a bore 124 of the first lateral distal arm 57 in order to lock the first lateral blade holder 83 and thus the first lateral blade holder assembly 82 to the first lateral distal arm 57. As illustrated in FIG. 23, a c-clip 123 is provided to prevent the first lateral blade lock bolt 60 from coming out after the first lateral blade holder assembly 82 is removed.

The first lateral blade 88 is elongated and generally curved having a generally curved convex distal face 90 and a generally curved concave proximal face 89. The curved convex distal face 90 is generally smooth but having a slot 91 at its top axially beneath the bore 87. The bore 87 and slot 91 is configured to accept an instrument (not shown) that may aid in retraction. The curved concave proximal face 89 has various grooves or slots. Central dovetail configured slot 92 extending axially from the first lateral blade holder 83 to almost near a distal end 94 of the first lateral blade 88, accepts a light source cable (not shown) that can go down the dovetail to provide light into the disc space, or a blade extender (not shown) which may also interface with the other features. The dovetail slot 92 may include an interface 95 for connection purposes. Rounded slot 93 extends axially from the first lateral blade holder 83 to almost near the distal end 94. The rounded slot 93 accepts another light source cable (not shown) or other instrument (not shown).

The second lateral blade holder assembly 96 includes a second lateral blade holder 97 and the second lateral blade 102 that extends from the second lateral blade holder 97. The second lateral blade holder 97 is configured as an elongated arm and includes a generally round boss 98 at one end having a threaded bore 99 extending therethrough, and a configured end 100 at another end opposite the boss 99 and having a bore 101 therethrough. The second lateral blade holder 97 is configured to be received in a like-configured notch 71 disposed in the underside of the distal end 62 of the second lateral distal arm 61. The threaded bore 99 receives a threaded shaft 64a of a second lateral blade lock bolt 64 extending through a bore (not seen) of the second lateral distal arm 61 in order to lock the second lateral blade holder 97 and thus the second lateral blade holder assembly 96 to the second lateral distal arm 61. A c-clip (not seen) is provided to prevent the second lateral blade lock bolt 64 from coming out after the second lateral blade holder assembly 96 is removed.

The second lateral blade 102 is elongated and generally curved having a generally curved convex distal face 104 and a generally curved concave proximal face 103. The curved convex distal face 104 is generally smooth but having a slot 105 at its top axially beneath the bore 101. The bore 101 and slot 105 is configured to accept an instrument (not shown) that may aid in retraction. The curved concave proximal face 103 has various grooves or slots. Central dovetail configured slot 106 extending axially from the second lateral blade holder 97 to almost near a distal end 108 of the second lateral blade 102, accepts a light source cable (not shown) that can go down the dovetail to provide light into the disc space, or a blade extender (not shown) which may also interface with the other features. The dovetail slot 106 may include an interface (not seen) for connection purposes. Rounded slot 107 extends axially from the second lateral blade holder 97 to almost near the distal end 108. The rounded slot 107 accepts another light source cable (not shown) or other instrument (not shown).

Figure 20:
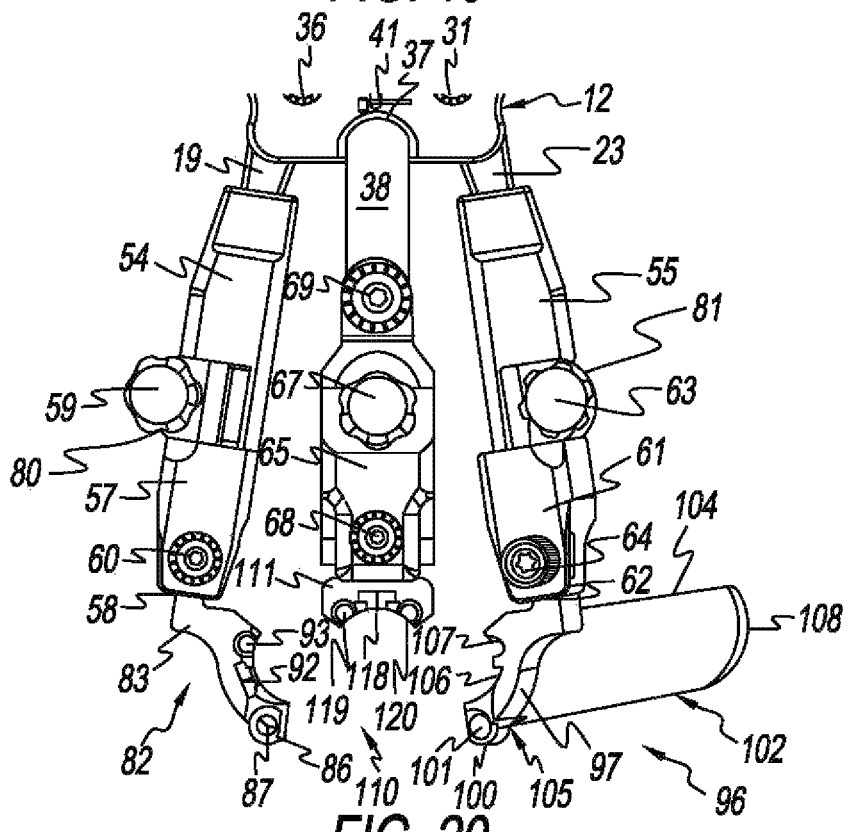
FIG. 20 is an enlarged top plan view of the blade holder assembly of the orthopedic retractor as depicted in FIG. 18.
Figure 21:
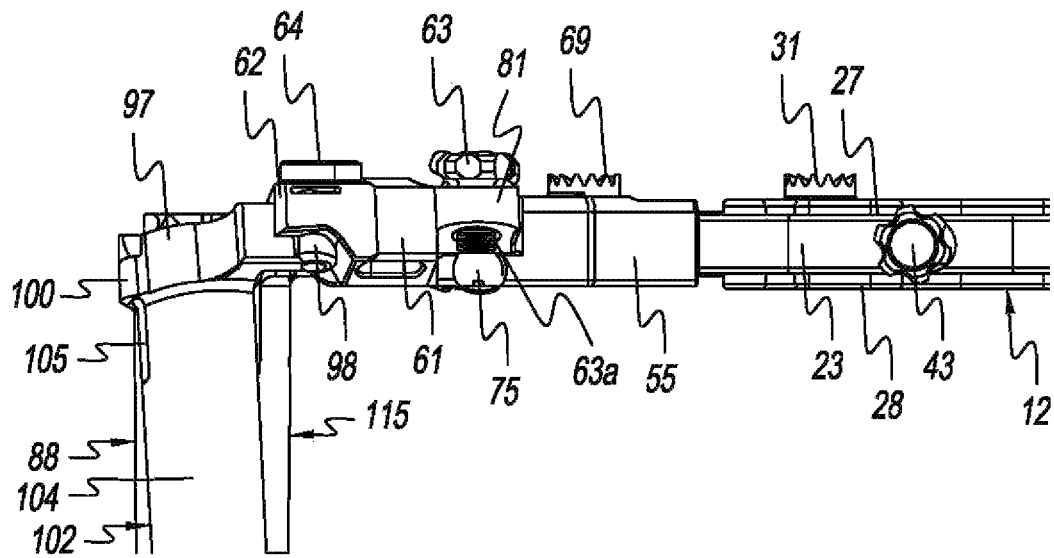
FIG. 21 is an enlarged side view of a portion of the blade holder assembly of the orthopedic retractor as depicted in FIG. 18.
Figure 22:
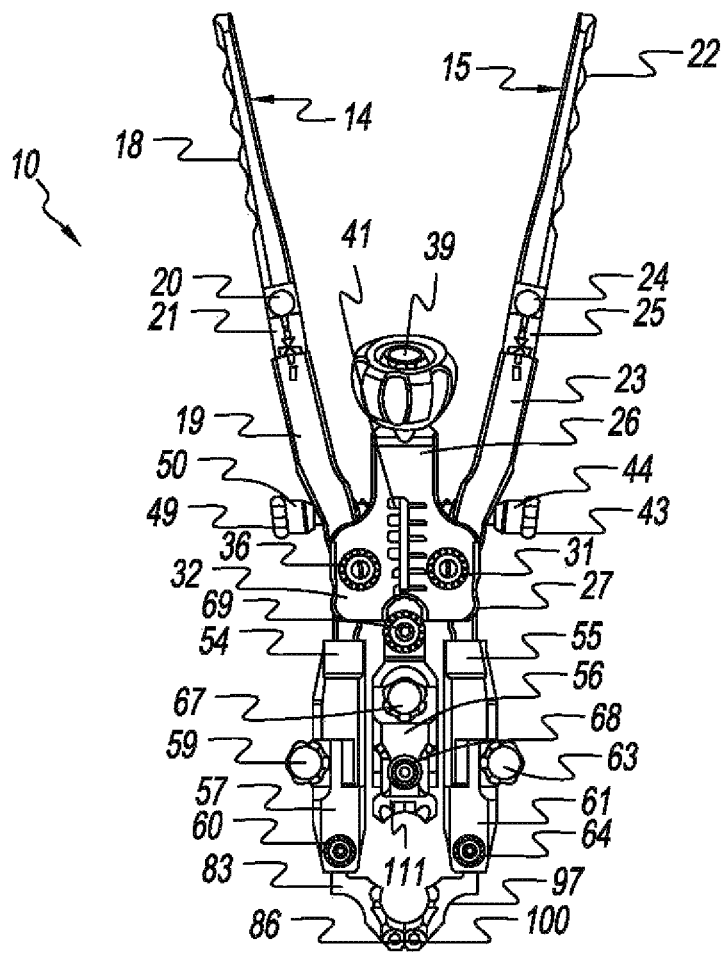
FIG. 22 is a top plan view of the orthopedic retractor of FIG. 1.

As seen in FIG. 20, the medial blade holder assembly 110 includes a medial blade holder 111 and the medial blade 115 that extends from the medial blade holder 111. The medial blade holder 111 is configured as an elongated arm and includes a generally round boss 113 in the middle of the medial blade holder 111 having a threaded bore 114 extending therethrough. The medial blade holder 111 is configured to be received in a like-configured notch 72 disposed in the underside of the distal end 66 of the medial distal arm 65. The threaded bore 114 receives a threaded shaft 68a of a medial blade lock bolt 68 extending through a bore (not seen) of the medial distal arm 65 in order to lock the medial blade holder 97 and thus the medial blade holder assembly 96 to the medial distal arm 65. Ac-clip (not seen) is provided to prevent the medial blade lock bolt 68 from coming out after the medial blade holder assembly 96 is removed.

Figure 19:
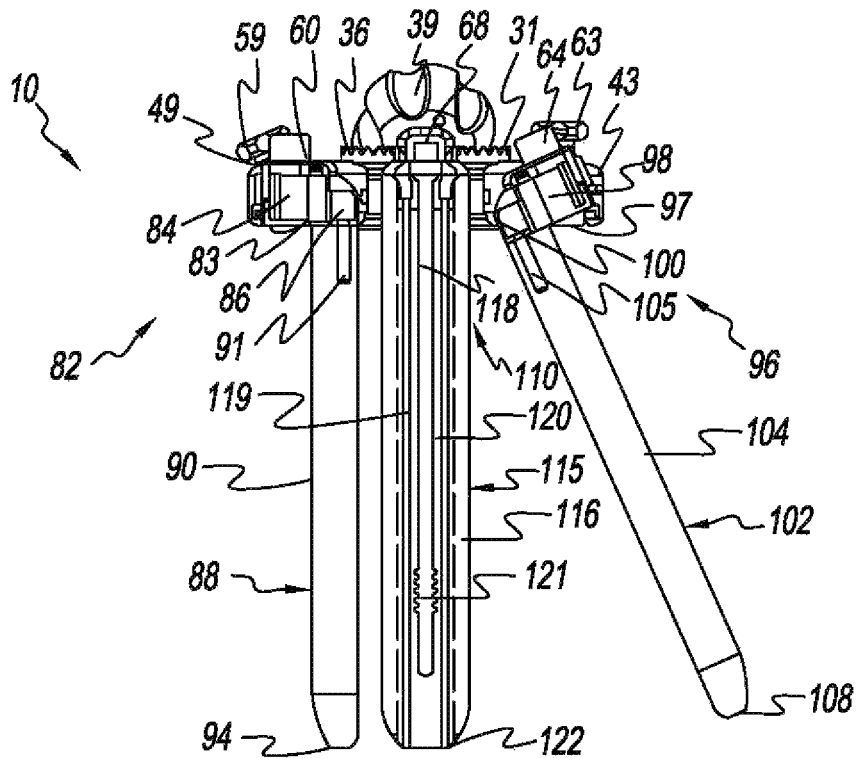
FIG. 19 is a front plan view of the orthopedic retractor as depicted in FIG. 18.

As seen in FIGS. 19 and 20, the medial blade is elongated and generally curved having a generally curved convex proximal face 117 and a generally curved concave distal face 116. The curved convex proximal face 117 is generally smooth. The curved concave distal face 116 has various grooves or slots. Central dovetail configured slot 118 extending axially from the medial blade holder 111 to almost near a distal end 122 of the medial blade 115, accepts a light source cable (not shown) that can go down the dovetail to provide light into the disc space, or a blade extender (not shown) which may also interface with the other features. The dovetail slot 118 may include an interface 121 for connection purposes. A first rounded medial slot 119 is disposed at one lateral side of the concave distal face 116 and extends axially from the medial blade holder 111 to almost near the distal end 122. A second rounded medial slot 120 is disposed at the other lateral side of the concave distal face 116 and extends axially from the medial blade holder 111 to almost near the distal end 122. The rounded slots 113, 120 accepts light source cables (not shown) or other instruments (not shown).

The present retractor 10 may be used for surgery other than procedures relating to the spine. Variations such as component size are contemplated as well as other manners or mechanisms for the features of the retractor presented herein.

It should furthermore be appreciated that dimensions of the components, structures, assemblies, and/or features of the present orthopedic retractor maybe altered as desired within the scope of the present disclosure.

The invention claimed is:

1. A retractor comprising:
   a body;
   a first handle having a first handle portion pivotally coupled to the body and a second handle portion detachably coupled to the first handle portion;
   a first attachment assembly comprising a first button configured to allow detachment of the second handle portion from the first handle portion in response to depressing the first button;
   a first arm assembly attached to the first handle;
   a first blade attached to the first arm assembly, wherein the first handle is configured to control distraction of the first blade relative to the body in response to pivotal motion of the first handle;
   a first angulation assembly comprising a first ball positioned within a first lateral pocket in the first arm assembly and a first bolt received in a first aperture on the first ball, wherein rotation of the first bolt is configured to adjust an angle of the first blade relative to the body;
   a second handle having a third handle portion pivotally coupled to the body and a fourth handle portion detachably coupled to the third handle portion;
   a second attachment assembly comprising a second button configured to allow detachment of the fourth handle portion from the third handle portion in response to depressing the second button;
   a second arm assembly attached to the second handle;
   a second blade attached to the second arm assembly, wherein the second handle is configured to control distraction of the second blade relative to the body in response to pivotal motion of the second handle; and
   a second angulation assembly comprising a second ball positioned within a second lateral pocket in the second arm assembly and a second bolt received in a second aperture on the second ball, wherein rotation of the second bolt is configured to adjust an angle of the second blade relative to the body.

2. The retractor of claim 1, further comprising:
   a third arm assembly attached to the body between the first arm assembly and the second arm assembly; and
   a third blade attached to the third arm assembly.

3. The retractor of claim 2, further comprising a drive assembly coupled to the third arm assembly, the drive assembly configured to control distraction of the third blade relative to the body.

4. The retractor of claim 3, wherein the drive assembly includes a threaded screw that is visible though a slot in the body, wherein rotation of the threaded screw causes a change in distraction of the third blade.

5. The retractor of claim 1, further comprising a first distraction control assembly coupled to the body and including a first bolt, wherein rotation of the first bolt causes a change in distraction of the first blade.

6. The retractor of claim 5, further comprising a second distraction control assembly coupled to the body and including a second bolt, wherein rotation of the second bolt causes a change in distraction of the second blade.

7. A retractor comprising:
   a body;
   a first handle having a first handle portion pivotally coupled to the body and a second handle portion detachably coupled to the first handle portion;
   a first arm assembly attached to the first handle;
   a first blade attached to the first arm assembly, wherein the first handle is configured to control distraction of the first blade relative to the body in response to pivotal motion of the first handle;
   a first angulation assembly comprising a first ball positioned within a first lateral pocket in the first arm assembly and a first bolt received in a first aperture on the first ball, wherein rotation of the first bolt is configured to adjust an angle of the first blade relative to the body;
   a second handle having a third handle portion pivotally coupled to the body and a fourth handle portion detachably coupled to the third handle portion; and a second arm assembly attached to the second handle;

a second blade attached to the second arm assembly, wherein the second handle is configured to control distraction of the second blade relative to the body in response to pivotal motion of the second handle; and a second angulation assembly comprising a second ball positioned within a second lateral pocket in the second arm assembly and a second bolt received in a second aperture on the second ball, wherein rotation of the second bolt is configured to adjust an angle of the second blade relative to the body.

8. The retractor of claim 7, further comprising:

a third arm assembly attached to the body between the first arm assembly and the second arm assembly; and a third blade attached to the third arm assembly.

9. The retractor of claim 8, further comprising a drive assembly coupled to the third arm assembly, the drive assembly configured to control distraction of the third blade relative to the body.

10. The retractor of claim 9, wherein the drive assembly includes a threaded screw that is visible though a slot in the body, wherein rotation of the threaded screw causes a change in distraction of the third blade.

* * * * *